United States Patent
Armstrong

Patent Number: 5,456,699
Date of Patent: Oct. 10, 1995

[54] CARDIAC STIMULATOR LEAD INSERTION TOOL

[75] Inventor: Randolph K. Armstrong, Missouri City, Tex.

[73] Assignee: Intermedics, Inc., Angleton, Tex.

[21] Appl. No.: 163,880

[22] Filed: Dec. 8, 1993

[51] Int. Cl.6 .................................................. A61M 5/00
[52] U.S. Cl. ........................................... 606/108; 607/37
[58] Field of Search ........................... 128/899; 604/263; 606/1, 108; 607/2, 36, 37, 115

[56] References Cited

U.S. PATENT DOCUMENTS

| | | | |
|---|---|---|---|
| 2,854,976 | 10/1958 | Heydrich | 604/263 |
| 3,658,061 | 4/1972 | Hall | 604/263 |
| 4,659,330 | 4/1987 | Nelson et al. | 604/263 |
| 4,759,363 | 7/1988 | Jensen | 128/305 |
| 4,795,443 | 1/1989 | Permenter et al. | 604/263 |
| 4,867,746 | 9/1989 | Dufresne | 604/263 |
| 5,013,310 | 5/1991 | Goode et al. | 606/1 |
| 5,050,602 | 9/1991 | Osypka | 128/419 |
| 5,070,605 | 12/1991 | Daglow et al. | 607/37 |

Primary Examiner—Stephen C. Pellegrino
Assistant Examiner—Nancy Mulcare
Attorney, Agent, or Firm—Richard L. Robinson

[57] ABSTRACT

A lead insertion tool for use with an implantable cardiac stimulator having a connector receptacle and for use with an associated lead having a connector pin for insertion within the connector receptacle. The tool includes spring biased jaws for gripping the lead at a location set back from the terminus of the connector pin. An insertion stop is connected to the jaw for engaging the cardiac stimulator to limit the depth of insertion of the connector pin within the connector receptacle. An integral depth gauge extends from the gripping jaws toward the terminus of the connector pin for gauging the location of the insertion stop relative to the terminus of the connector pin. Full insertion of the connector pin within the connector receptacle is assured when the insertion stop engages the cardiac stimulator. The depth gauge is hinged to the gripping jaws and can move out of the way as the connector pin is inserted into the connector receptacle.

11 Claims, 3 Drawing Sheets

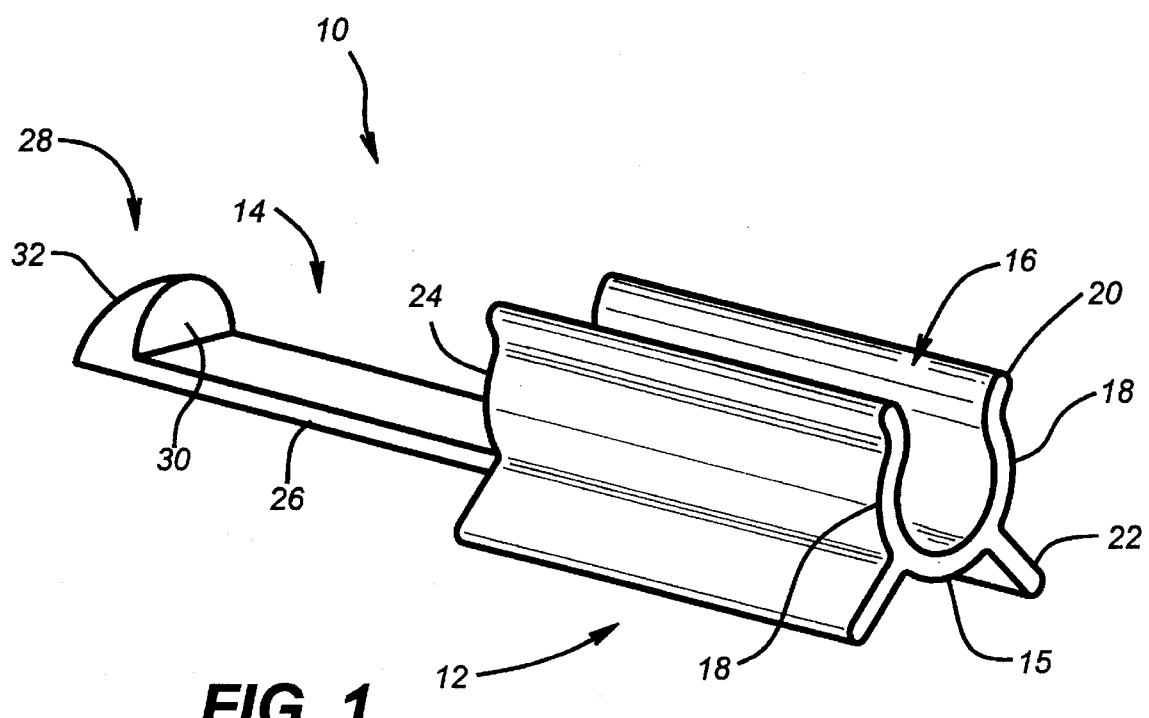
FIG. 1
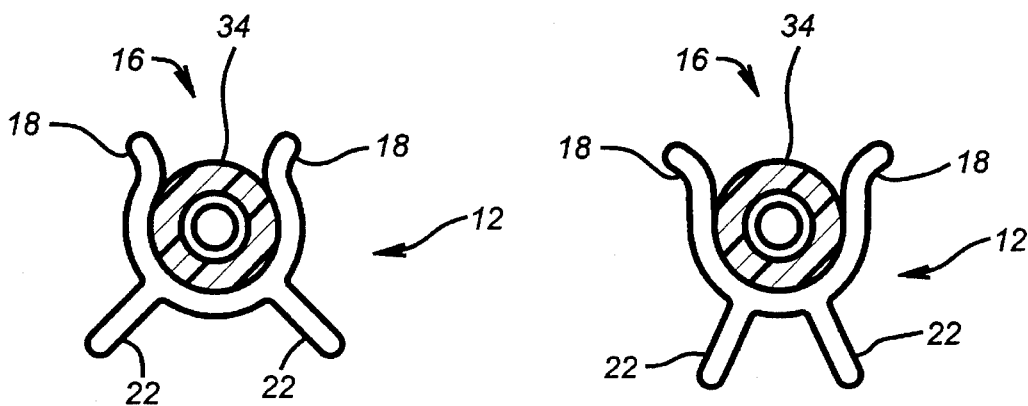
FIG. 2  FIG. 3

CARDIAC STIMULATOR LEAD INSERTION TOOL

BACKGROUND OF THE INVENTION

1. Field of the Invention

The present invention relates generally to implantable cardiac stimulators having one or more associated electrical leads that are insertable into an electrical connector in the cardiac stimulator, and relates more particularly to a tool for assisting in the insertion of the lead and for ensuring that the lead is fully inserted into the connector.

2. Background Information

Implantable cardiac stimulators generally include signal sensing, telemetry, and electrical stimulus generating circuitry, as well as a battery and other components that are hermetically sealed within a metal housing or "can." At least one electrically conducting lead having one or more electrodes designed for endovascular insertion within one or more chambers of the heart is provided externally of the metal housing. Typically, electrical connection between the circuit located within the can and the external electrically conducting lead is accomplished via a connectable and disconnectable electrical connector. The female portion of the connector, sometimes known as a connector block, is often embedded within a nonconducting transparent epoxy header attached to the outside of the metal housing. The connector block communicates with the exterior of the header via a passageway molded within the header. The connector block is electrically connected to the circuitry located within the metal housing via hermetic insulated feedthroughs located in the wall of the metal housing and extending into the epoxy header. The male portion of the connector, sometimes known as a connector pin, is attached to a proximal end of the lead and is configured to be received through the molded passageway into the connector block. Mechanical and electrical connection between the connector pin and the connector block is assured by a set screw in the connector block.

During implantation of the cardiac stimulator in a patient, the distal end of the lead including the electrodes is first implanted via an endovascular route into the interior of the heart. The cardiac stimulator is then implanted in a subcutaneous pocket and the proximal end of the lead is connected to the header of the cardiac stimulator. During insertion of the connector pin of the lead into the connector block of the cardiac stimulator, the physician usually looks into the transparent header to observe the progress of the connector pin, and can visually verify that the connector pin of the lead has been fully inserted into the connector block.

It has been suggested that implantable cardiac stimulators could be made smaller and more compact if the epoxy header were eliminated and the female portion of the connector were contained within the metal housing, with the connector being hermetically separated from the remainder of the interior of the metal housing. Such an arrangement might be described as a "headerless" cardiac stimulator. Because the metal housing is opaque, insertion of the connector pin of the lead within the cardiac stimulator connector could not be visually verified in such a headerless cardiac stimulator. Thus, the adoption of a headerless configuration for a cardiac stimulator would give rise to a need for a way to ensure that the connector pin of the lead is fully inserted. The present invention addresses and fulfills that need.

SUMMARY OF THE INVENTION

In accordance with one aspect of the present invention, a lead insertion tool is presented for use with an implantable cardiac stimulator and an associated lead. The cardiac stimulator has a connector receptacle for receiving a connector pin of the lead. The lead insertion tool includes gripping means having jaws for gripping the lead at a location set back from the terminus of the connector pin. An insertion stop means is connected to the gripping means for engaging the cardiac stimulator to limit the depth of insertion of the connector pin within the connector receptacle. A depth gauge means extends from the gripping means toward the terminus of the connector pin for gauging the location of the insertion stop means relative to the terminus of the connector pin such that full insertion of the connector pin within the connector receptacle is assured when the insertion stop engages the cardiac stimulator.

It is an object of the present invention to provide an instrument for assisting the insertion of a lead connector into a connector receptacle of a cardiac stimulator and for assuring that the lead connector is fully inserted regardless of whether the lead connector tip is visible during insertion.

Other objects and advantages of the present invention will be apparent from the following descriptions of preferred embodiments of the invention made with reference to the drawings.

BRIEF DESCRIPTION OF THE DRAWINGS

FIG. 1 is a perspective view of a first embodiment of a lead insertion tool configured in accordance with the present invention.

FIG. 2 is an end view of the lead insertion tool of FIG. 1 shown in a first closed configuration relative to a lead.

FIG. 3 is an end view of the lead insertion tool of FIG. 1 shown in a second open configuration relative to a lead.

DESCRIPTION OF THE PREFERRED EMBODIMENTS

Figure 4:
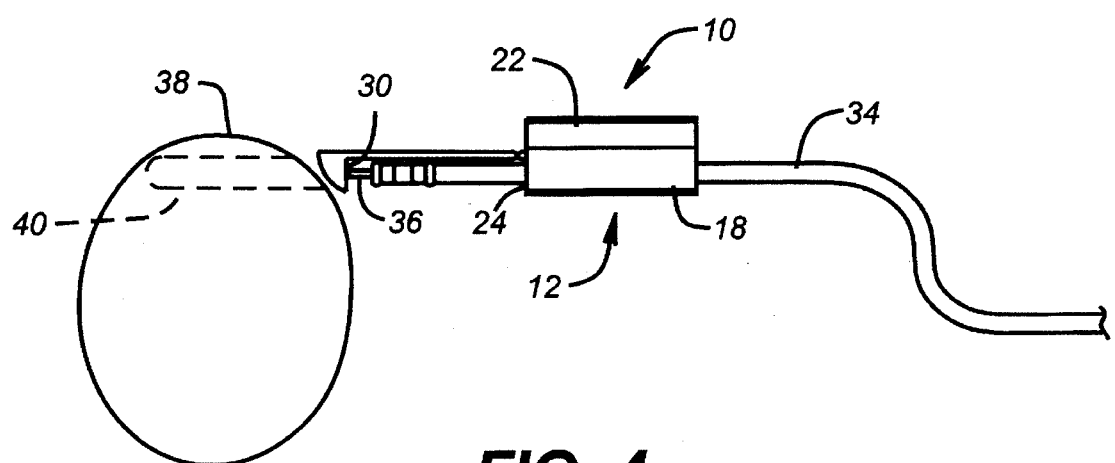
FIG. 4 is a side view of the lead insertion tool of FIG. 1 shown in use with a cardiac stimulator and associated lead.

Referring in particular to FIG. 1, there is illustrated a lead insertion tool 10 constructed in accordance with the present invention. Tool 10 is preferably an integral injection molded plastic part configured generally as a spring clamp. Tool 10 includes a main body 12 and a depth gauge 14.

Main body 12 is configured in its relaxed state as an elongate cylinder 15 open at both ends and having an open slot 16 extending the length thereof to define a pair of jaws 18 on each side of slot 16. Each jaw 18 terminates in a lip 20 that extends generally radially outwardly from cylinder 15 to facilitate entry of a lead therebetween through slot 16. A pair of wings 22 extend generally radially outwardly from cylinder 15 on the side generally opposite slot 16. Each wing 22 also extends the full length of cylinder 15 parallel thereto. In the relaxed state of main body 12, wings 22 extend outwardly along radii that are subtended by an angle of approximately 90°. One end face of cylinder 15 of main body 12 serves as an insertion stop 24 having a function described below. Depth gauge 14 is configured as an elongate tab 26 extending integrally from the insertion stop end face 24 of cylinder 15 proximate that side of cylinder 15 that is opposite open slot 16. Elongate tab 26 extends from insertion stop end face 24 at a location between the intersections of each of wings 22 with cylinder 15. Elongate tab 26 extends away from main body 12 and generally parallel to cylinder 15. Depth gauge 14 has a free end 28 at which a gauge stop 30 is located that extends perpendicularly from elongate tab 26 and radially inwardly relative to cylinder 15. On that side of gauge stop 30 that faces away from main body 12, depth gauge 14 includes a ramp surface 32 having a function described below.

Referring to FIGS. 2 and 3, there are illustrated end views of main body 12 of insertion tool 10 showing its gripping and open configurations, respectively, relative to a lead 34 received therewithin. In FIG. 2, main body 12 is shown with jaws 18 gripping lead 34. The inner diameter of main body 12 in its relaxed state is somewhat smaller than the outer diameter of lead 34. Thus, as shown in FIG. 2, main body 12 is in a state of spring tension which urges jaws 18 toward one another to grip lead 34. The spring tension is sufficient to prevent main body 12 from slipping relative to lead 34, particularly when main body 12 is grasped manually by the physician during use as is described below. As shown in FIG. 3, main body 12 is in a state of greater spring tension than in FIG. 2, due to wings 22 having been grasped by the physician and squeezed toward one another to elastically expand cylinder 15, causing jaws 18 to move apart from one another, thereby resulting in slot 16 opening sufficiently to permit lead 34 to be received therethrough. With jaws 18 in the open orientation shown in FIG. 3, main body 12 can be placed about lead 34, or lead 34 can be removed therefrom.

Figure 5:
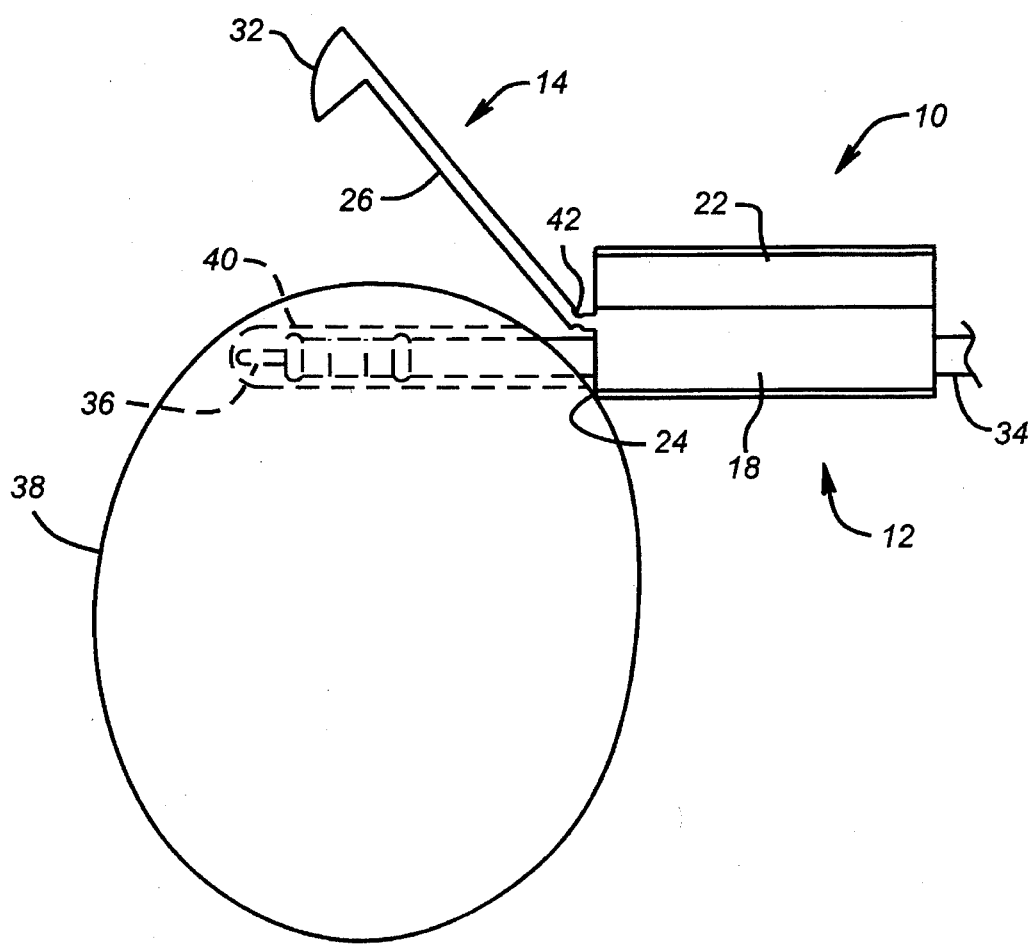
FIG. 5 is another side view of the lead insertion tool of FIG. 1 shown in use with a cardiac stimulator and associated lead.
Figure 6:
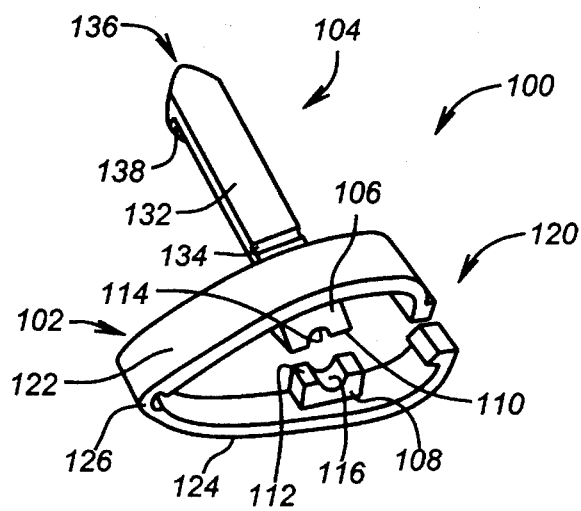
FIG. 6 is a perspective view of a second embodiment of a lead insertion tool configured in accordance with the present invention.
Figure 7:
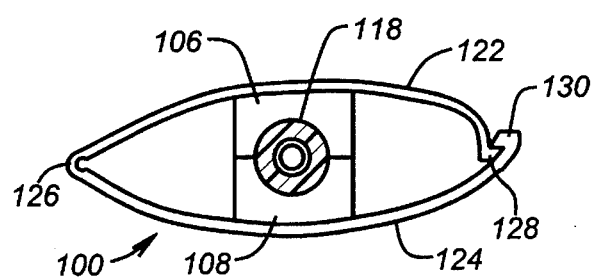
FIG. 7 is a side view of the lead insertion tool of FIG. 6.
Figure 8:
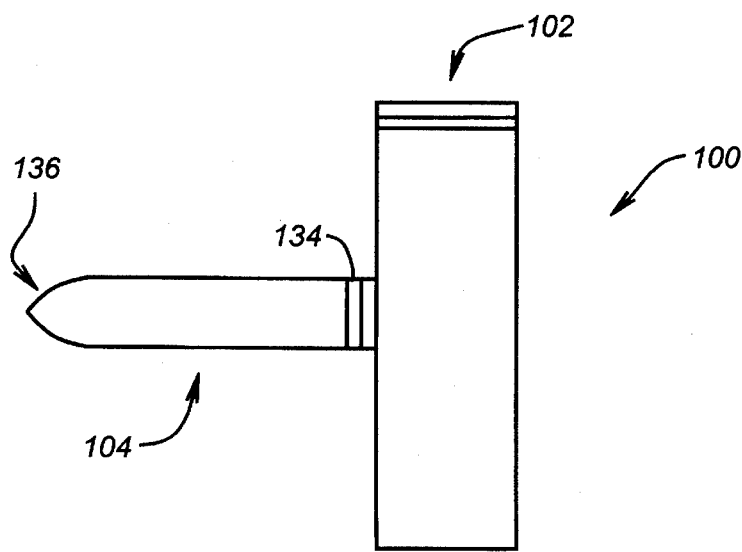
FIG. 8 is a plan view of the lead insertion tool of FIG. 6.
Figure 9:
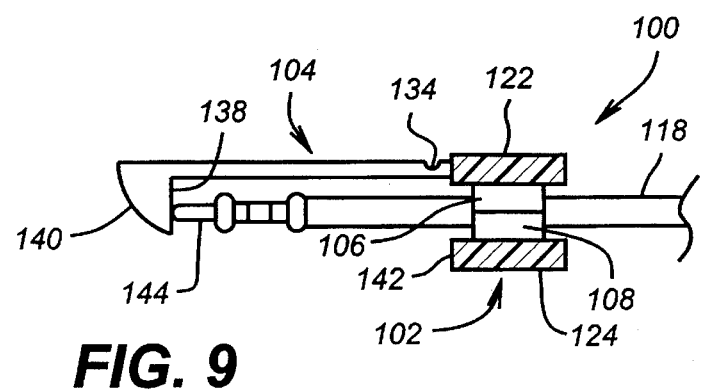
FIG. 9 is an end view shown partly in section of the lead insertion tool of FIG. 6, showing the tool in use with a lead.

Referring to FIGS. 4 and 5, lead insertion tool 10 is shown in use. Referring now to FIG. 4, the physician grasps wings 22 and squeezes them toward one another thereby opening jaws 18 as described above. While continuing to squeeze wings 22 to hold jaws 18 open, main body 12 of lead insertion tool 10 is placed over lead 34 such that lead 34 is received through slot 16 and between jaws 18. Main body 12 is then moved axially with respect to lead 34 as needed to cause gauge stop 30 to engage the terminus of connector pin 36 of lead 34. While maintaining gauge stop 30 in contact with the terminus of connector pin 36, wings 22 are released, allowing jaws 18 to spring back toward one another and grip lead 34 in spring tension. When so positioned, jaws 18 of main body 12 grip lead 34 at a location set back from the terminus of connector pin 36. The set back as determined by the length of depth gauge 14 is calculated to place insertion stop 24 at a position on lead 34 relative to the terminus of connector pin 36 such that the physician is assured that connector pin 36 is fully inserted within cardiac stimulator 38 when insertion stop 24 engages the outer surface of cardiac stimulator 38 as connector pin 36 is inserted within a corresponding connector receptacle 40 of cardiac stimulator 38.

Referring now to FIG. 5, use of lead insertion tool 10 is described further. Depth gauge 14 includes a hinge portion 42 of reduced thickness proximal to the point of connection between elongate tab 26 and main body 12 which allows depth gauge 14 to bend in response to forces directed transversely thereto. Such transverse forces can be generated by ramp surface 32 of depth gauge 14 as lead insertion tool 10, together with lead 34 gripped therewithin, is moved axially toward cardiac stimulator 38. As connector pin 36 enters connector receptacle 40, ramp surface 32 engages the outer surface of cardiac stimulator 38 adjacent the opening of connector receptacle 40 and causes depth gauge 14 to bend at hinge 42. Alternatively, the physician can manually bend depth gauge 14 out of the way prior to inserting connector pin 36 into connector receptacle 40. As the physician grasps main body 12 about the jaws 18 thereof, he inevitably squeezes the jaws 18 toward one another, thereby contributing to the grip that jaws 18 place on lead 34 and further ensuring that jaws 18 frictionally engage lead 34 sufficiently to prevent lead insertion tool 10 from moving relative to lead 34 as connector pin 36 is inserted. Once insertion stop 24 engages the outer surface of cardiac stimulator 38 adjacent the opening of connector receptacle 40, the physician is assured that connector pin 36 has been fully inserted even if the position of the terminus of connector pin 36 cannot be directly visually verified. Once connector pin 36 is fully inserted, lead insertion tool 10 can be removed from lead 34 by again squeezing wings 22 toward one another to open jaws 18 as described above.

Referring to FIGS. 6–9, there is illustrated an alternative embodiment of a lead insertion tool 100 constructed in accordance with the present invention. Lead insertion tool 100 includes a main body 102 and a depth gauge 104 and is preferably constructed as an integral one-piece plastic part formed by injection molding.

Main body 102 includes a pair of jaws 106 and 108 having mating surfaces 110 and 112, respectively. Formed in mating surfaces 110 and 112 are semi-cylindrical grooves 114 and 116 which, when mating surfaces 110 and 112 are in engagement, join to form a cylindrical channel for receiving a lead 118 therewithin. The cylindrical channel formed by semi-cylindrical grooves 114 and 116 is designed to have a diameter somewhat less than the diameter of lead 118 so that as jaws 106 and 108 are pressed toward one another they frictionally grip lead 118 via grooves 114 and 116.

In distinction from the first embodiment described above, the embodiment of FIGS. 6–9 limits the maximum compressive force applied to lead 118 by virtue of the fact that mating surfaces 110 and 112 of jaws 106 and 108 limit movement of jaws 106 and 108 toward one another. In other words, as mating surfaces 110 and 112 engage, lead 118 is prevented from being subjected to any greater compression than that designed into insertion tool 100 by virtue of the undersizing of the cylindrical channel formed by semi-cylindrical grooves 114 and 116 relative to the diameter of lead 118. This arrangement has the advantage of preventing the lead 118 from being inadvertently crushed by overzealous squeezing of the insertion tool during insertion of the lead into the cardiac stimulator.

Jaws 106 and 108 are integral with a spring clip 120 including two spring leaves 122 and 124 joined at one end by a hinge portion 126 of reduced thickness and having lips 128 and 130 at the other end configured to overlap one another and hold spring clip 120 closed.

Depth gauge 104 is configured as an elongate tab 132 having a hinge portion 134 of reduced thickness proximal the point of attachment of elongate tab 132 to spring leaf 122. Elongate tab 132 extends perpendicularly away from spring clip 120 and generally parallel to the cylindrical channel formed by semi-cylindrical grooves 114 and 116. Depth gauge 104 has a free end 136 at which a gauge stop 138 is located that extends perpendicularly from elongate tab 132 and radially inwardly relative to the cylindrical channel formed by semi-cylindrical grooves 114 and 116. On that side of gauge stop 138 that faces away from main body 102, depth gauge 104 includes a ramp surface 140 that serves essentially the same function as ramp surface 32 of the first embodiment of FIG. 1. Edge 142 of spring leaf 124 on the side of spring leaf 124 that faces depth gauge 104 serves as an insertion stop in the same manner as insertion stop 24 of the first embodiment of FIG. 1.

Lead insertion tool 100 is used in substantially the same manner as lead insertion tool 10 of the first embodiment illustrated in FIGS. 1-5, except that jaws 106 and 108 are opened by disengaging overlapping lips 128 and 130 from one another and moving spring leaves 122 and 124 apart about hinge 126. The lead 118 is inserted within semi-cylindrical channels 114 and 116 and the terminus of connector pin 144 of lead 118 is engaged with gauge stop 138 of depth gauge 104. Spring leaves 122 and 124 are then squeezed together until lips 128 and 130 engage and overlap one another. When lips 128 and 130 are so engaged, each of spring leaves 122 and 124 are in spring tension and urging jaws 106 and 108 toward one another. Lead 118 is compressed slightly therebetween as mating surfaces 110 and 112 of jaws 106 and 108 engaged each other. At that point, main body 102 of lead insertion tool 1 00 is frictionally engaged with lead 118 in such a location that insertion stop edge 142 is set back from the terminus of connector pin 144 a distance calculated in ensure that connector pin 144 is fully inserted within a corresponding connector receptacle of an associated cardiac stimulator when insertion stop edge 142 engages the outer surface of the cardiac stimulator during insertion of connector pin 144 therein.

While the present invention has been illustrated and described with particularity in terms of preferred embodiments, it should be understood that no limitation of the scope of the invention is intended thereby. The scope of the invention is defined only by the claims appended hereto. It should also be understood that variations of the particular embodiments described herein incorporating the principles of the present invention will occur to those of ordinary skill in the art and yet be within the scope of the appended claims. It should further be appreciated that while the present invention has been disclosed as having particular advantages when used with a headerless cardiac stimulator or otherwise opaque connector receptacle of a cardiac stimulator, the invention is nevertheless also useful when used with a cardiac stimulator having a conventional transparent header.

What I claim is:

1. A lead insertion system having a lead insertion tool, an implantable cardiac stimulator having a connector receptacle, and an associated lead having a connector pin for insertion within said connector receptacle, said connector pin having a terminus, said lead insertion tool comprising:

gripping means having jaws for gripping said lead at a location set back from the terminus of said connector pin;

insertion stop means connected to said jaws of said gripping means for engaging said cardiac stimulator to limit the depth of insertion of said connector pin within said connector receptacle; and depth gauge means connected to and extending from said jaws of said gripping means toward the terminus of said connector pin for gauging the location of said insertion stop means relative to the terminus of said connector pin such that full insertion of said connector pin within said connector receptacle is assured when said insertion stop engages said cardiac stimulator.

2. The lead insertion tool of claim 1, in which said gripping means includes means for urging said jaws toward said lead under spring tension.

3. The lead insertion tool of claim 2, in which said means for urging said jaws toward said lead under spring tension includes a cylinder having an opening along one side for receiving said lead therewithin, each of said jaws comprising a portion of said cylinder to one side of said opening.

4. The lead insertion tool of claim 2, in which said means for urging said jaws toward said lead under spring tension includes a pair of spring leaves hingedly connected to one another at one end and engagable and disengable at another end, with said jaws disposed between said pair of spring leaves.

5. The lead insertion tool of claim 1, in which said jaws of said gripping means include means for limiting movement of said jaws toward one another to prevent excessive compression of a lead received therebetween.

6. The lead insertion tool of claim 1, in which said depth gauge means is hingedly attached to said gripping means.

7. The lead insertion tool of claim 6, in which said depth gauge means has a free end and means at said free end for hingedly moving said depth gauge upon engagement of said free end with an outer surface of said cardiac stimulator.

8. The lead insertion tool of claim 7, in which said means for hingedly moving includes a ramp surface at said free end.

9. The lead insertion tool of claim 1, in which said depth gauge means has a free end and a gauge stop at said free end extending substantially perpendicular to said depth gauge.

10. A lead insertion tool for use with an implantable cardiac stimulator having a connector receptacle and for use with an associated lead having a connector pin for insertion within said connector receptacle, said connector pin having a terminus, comprising:

gripping means having jaws for gripping said lead at a location set back from the terminus of said connector pin, said gripping means including means for urging said jaws toward said lead under spring tension, said means for urging including a pair of spring leaves hingedly connected to one another at one end and engagable and disengagable at another end, with said jaws disposed between said pair of spring leaves;

insertion stop means connected to said jaws of said gripping means for engaging said cardiac stimulator to limit the depth of insertion of said connector pin within said connector receptacle; and depth gauge means connected to and extending from said jaws of said gripping means toward the terminus of said connector pin for gauging the location of said insertion stop means relative to the terminus of said connector pin such that full insertion of said connector pin within said connector receptacle is assured when said insertion stop engages said cardiac stimulator.

11. A method of inserting a lead into an associated implantable cardiac stimulator, comprising the steps of:

a) providing a lead having a connector pin, said connector pin having a terminus;

b) providing an implantable cardiac stimulator associated with said lead, said implantable cardiac stimulator having a connector receptacle;

c) providing a lead insertion tool having:

gripping means having jaws for gripping said lead at a location set back from the terminus of said connector pin;

insertion stop means connected to said jaws of said gripping means for engaging said implantable cardiac stimulator to limit depth of insertion of said connector pin within said connector receptacle; and depth gauge means connected to and extending from said jaws of said gripping means toward the terminus of said connector pin for gauging the location of said insertion stop means relative to the terminus of said connector pin such that full insertion of said connector pin within said connector receptacle is assured when said insertion stop engages said cardiac stimulator;

d) gripping said lead with said jaws of said gripping means of said lead insertion tool at a location set back from the terminus of said connector pin such that said depth gauge means contacts the terminus of said connector pin, thereby gauging the location of said insertion stop means relative to the terminus of said connector pin; and e) inserting said connector pin of said lead into the connector receptacle of said implantable cardiac stimulator until said insertion stop means engages said implantable cardiac stimulator, whereby full insertion of said connector pin within said connector receptacle is assured.

* * * * *